(12) United States Patent
Maher et al.

(10) Patent No.: US 9,992,978 B2
(45) Date of Patent: Jun. 12, 2018

(54) OXALIC ACID VAPORIZER

(71) Applicant: Miller Manufacturing Company, Eagan, MN (US)

(72) Inventors: Michael Detrich Maher, Darwin, MN (US); Brady A. LaMott, St. Bonifacius, MN (US)

(73) Assignee: Miller Manufacturing Company, Eagan, MN (US)

( * ) Notice: Subject to any disclaimer, the term of this patent is extended or adjusted under 35 U.S.C. 154(b) by 334 days.

(21) Appl. No.: 14/988,315

(22) Filed: Jan. 5, 2016

(65) Prior Publication Data
US 2017/0188550 A1 Jul. 6, 2017

(51) Int. Cl.
*A01K 51/00* (2006.01)
*A01M 13/00* (2006.01)
*A01M 1/20* (2006.01)
*A01N 37/04* (2006.01)

(52) U.S. Cl.
CPC ........... *A01K 51/00* (2013.01); *A01M 1/2077* (2013.01); *A01M 13/00* (2013.01); *A01N 37/04* (2013.01)

(58) Field of Classification Search
CPC ..... A01K 51/00; A01K 55/00; A01M 1/2077; A01M 13/00; A01N 37/04
See application file for complete search history.

(56) References Cited

U.S. PATENT DOCUMENTS

| 5,282,334 A * | 2/1994 | Kimura | A01M 1/2072 261/DIG. 89 |
| 5,335,446 A * | 8/1994 | Shigetoyo | A01M 1/2033 43/125 |
| 8,296,993 B2 * | 10/2012 | Modlin | A01M 29/12 239/102.2 |
| 8,353,126 B2 * | 1/2013 | Stearns | A01K 55/00 43/127 |

(Continued)

FOREIGN PATENT DOCUMENTS

| DE | 10054048 A1 * | 5/2002 | ............. A01K 51/00 |
| DE | 202007002266 U1 * | 4/2007 | ............. A01K 51/00 |
| DE | 202007001721 * | 7/2007 | ............. A01K 51/00 |

OTHER PUBLICATIONS

Machine translation of DE 10054048.*

(Continued)

*Primary Examiner* — Kathleen I Alker
(74) *Attorney, Agent, or Firm* — Briggs and Morgan, P.A.; Gerald E. Helget

(57) ABSTRACT

An oxalic acid vaporizer for vaporizing oxalic acid crystals in a bee hive with a bee entrance for treatment to kill mites on bees and in the bee hive has a cup to hold oxalic acid crystals with a resistive heating element mounted on one end of an extension. A handle is mounted on the other end of an extension with internal resistive heating element wires passing from the heating element to an internal circuit board with a microcontroller. A rocker switch is mounted on the handle connected to the circuit board. An LED is mounted to the (Continued)

handle connected to the circuit board. An external electrical cord connected to the circuit board and extending out of the handle with a positive battery post clamp and a negative battery post clamp is adaptable to be connected to a 12 volt battery.

2 Claims, 3 Drawing Sheets

(56) References Cited

U.S. PATENT DOCUMENTS

| | | | |
|---|---|---|---|
| 8,430,337 B2* | 4/2013 | Pearce | A01G 13/06 239/457 |
| 2008/0056691 A1* | 3/2008 | Wingo | A01M 1/2033 392/395 |
| 2010/0059601 A1* | 3/2010 | Bankers | A01M 1/2077 239/44 |
| 2011/0253798 A1* | 10/2011 | Tucker | A61L 9/037 239/13 |

OTHER PUBLICATIONS

Machine translation of DE 202007002266.*
Machine translation of DE 202007001721.*
Berry, Oxalic Acid: Effective & Easy on Bees, But, Bee Culture, http://www.beeculture.com/oxalic-acid-effective-easy-on-bees-but/, May 25, 2015, pp. 1-11.
Varrocleaner, OxaVap—Your Source for Oxalic Acid Vaporizers, https://oxavap.com/product/varrocleaner-oxalic-acid-vaporizer/, Dec. 9, 2015, pp. 1-3.
Google Search, Oxalic Acid Vaporizer pictures, Dec. 9, 2015, pp. 1-7.
Bedillion Honey Farm & Farm Market, Heilyser Oxalic Acid Vaporizer, http://www.bedillionhoneyfarm.com/store/heilyser-oxalic-acid-vaporizer-heilyser-oxalic-acid-vaporizer, Dec. 9, 2015, pp. 2/4-3/4.
Scientific Beekeeping.com, Oxalic Acid: Heat Vaporization and Other Methods: Part 2 of 2 Parts, http://scientificbeekeeping.com/oxalic-acid-heat-vaporization-and-other-methos-part-2-of-2-parts, 2007, pp. 1/11-7/11.

* cited by examiner

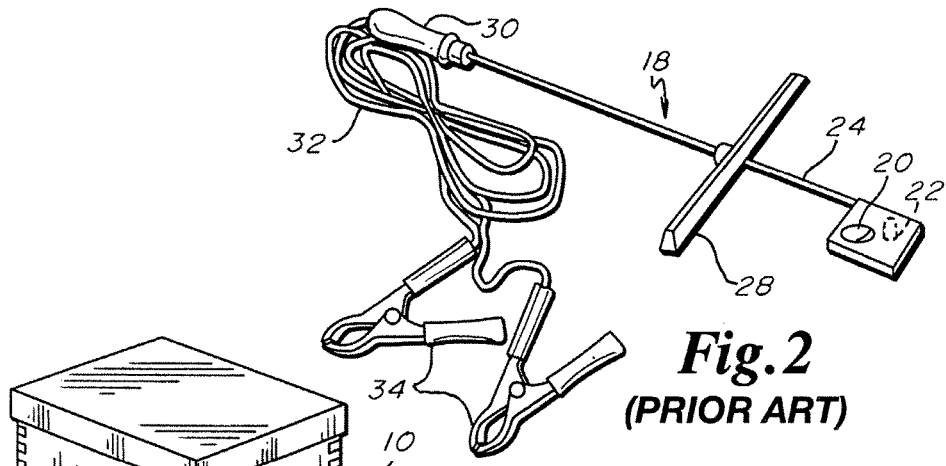
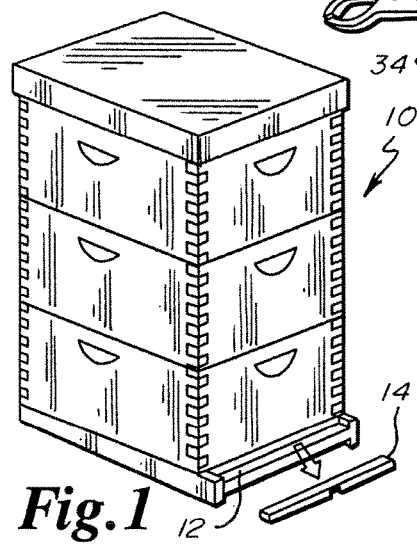
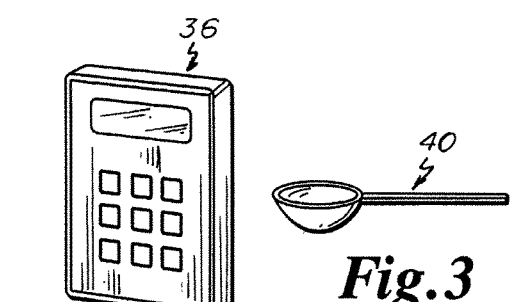
*Fig.1* (PRIOR ART)    *Fig.2* (PRIOR ART)    *Fig.3* (PRIOR ART)    *Fig.4* (PRIOR ART)
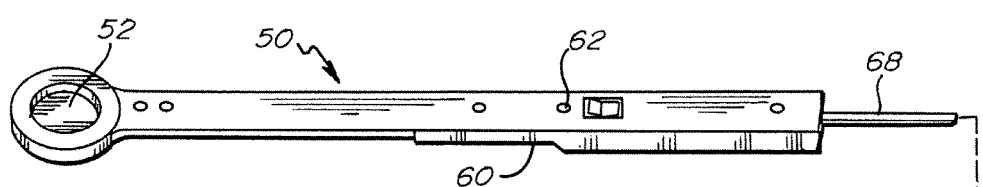
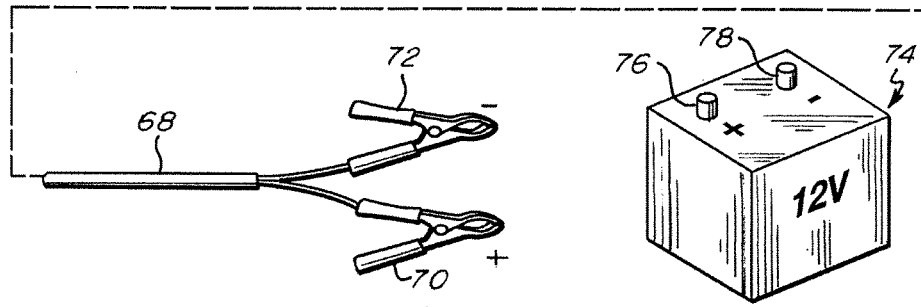
*Fig.5*

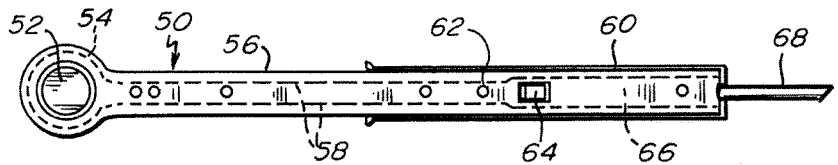
*Fig.6*
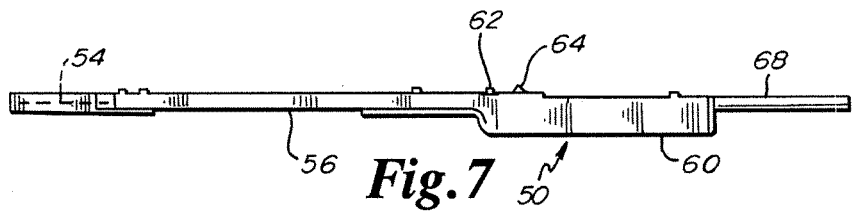
*Fig.7*
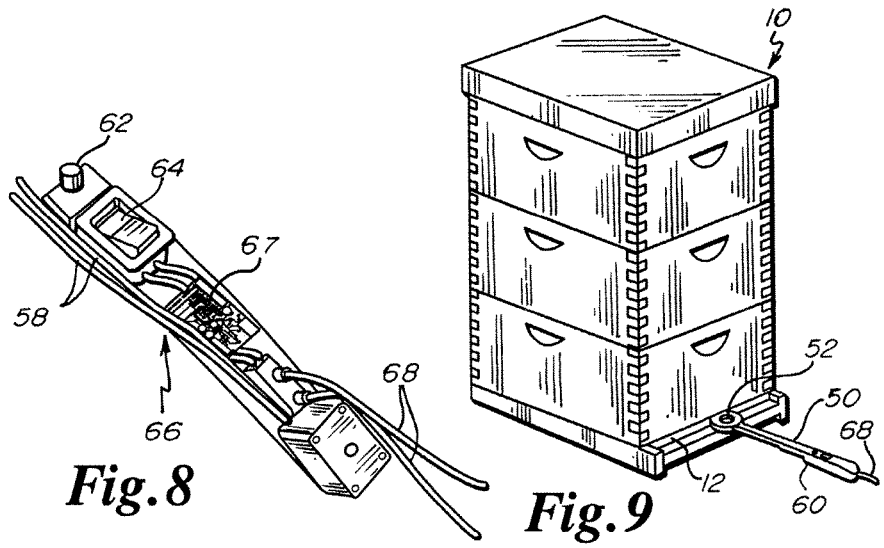
*Fig.8*
*Fig.9*
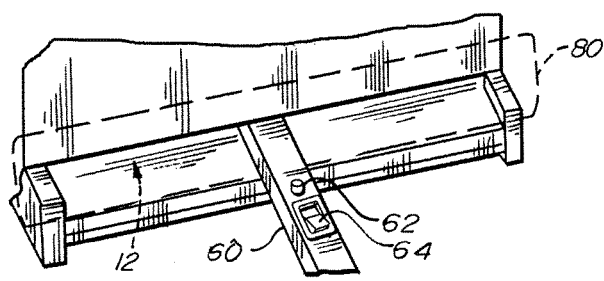
*Fig.10*

OXALIC ACID VAPORIZER

BACKGROUND OF THE INVENTION

The present invention relates the keeping of honey bees in bee hives, and more particularly to, maintaining the health of the bees with oxalic acid vaporization in the hive which kills *Varroa* and Tracheal mites that are detrimental to the health of the bees without harming the bees.

Prior art FIG. 1 shows a typical honey bee hive 10. The bees come out of and enter into the bee hive 10 through entrance/exit 12 which typically has a removable reducer 14. Inside the hive are honeycombs. Honey gets its start as flower nectar, which is collected by bees, naturally breaks down into simple sugars and is stored in honeycombs. The unique design of the honeycomb, coupled with constant fanning by the bees' wings, causes evaporation to take place, creating the thick, sweet liquid known as honey.

In the mid-1980s, the number one destructive pest of the western honey bee (*Apis mellifera*), the parasitic mite *Varroa destructor*, was introduced to the United States and has since spread to almost all honey bee colonies in North America. *Varroa* was first detected on western honey bees back in the 1950s. It now is present in most areas of the world where the western honey bee is present, as a result of natural migration, but most actively with assistance from humans who move bees for trade both legally and illegally It is now difficult to find a "*varroa*-free" western honey bee colony anywhere except for Australia and Newfoundland in Canada, and possibly a few other isolated island locations.

*Varroa* mites are external honeybee parasites that attack both the adults and the brood, with a distinct preference for drone brood. They suck the blood from both the adults and the developing brood, weakening and shortening the life span of the ones on which they feed. Emerging brood may be deformed with missing legs or wings. Untreated infestations of *varroa* mites that are allowed to increase will kill honeybee colonies.

Prior art FIG. 2 shows a typical prior art oxalic acid vaporizer 18 for bee hives 10. The vaporization of oxalic acid in bee hives is a proven method of killing both *Varroa* & Tracheal mites. This vaporizer 18 typically comes with a cup or crucible 20 for heating and vaporizing oxalic acid by heating the cup 20 with a heating element 22, such as a diesel glow plug. The cup 20 is mounted on a rod 24 with internal wires (not shown). A handle 30 is provided for gripping the vaporizer 18 and an external cord 32 connected to the internal wires terminates in battery post clamps 34.

In operation, simply load the cup 20 of the vaporizer 18 with one gram (per deep box) of oxalic acid (HOOCCOOH) by use of a one gram scoop 40 (FIG. 3). Next, remove the entrance reducer 14 and insert the cup 20 into the hive 10 up to the entrance block 28 and connect the battery clamps 34 to any 12 volt, 12 amp battery. The vaporization will complete in about 2.5 minutes. Thereafter, the battery clamps 34 must be removed from the battery. The bee keeper must have a timer 36 (FIG. 4) as to not leave the vaporizer 18 on for too long which may cause a burning of the acid, the hive, fire in the hive 10 or death of bees. The vaporizer 18 is left in the hive for some additional time ranging from a minute up to ten minutes to seal in the vapors. The timer 36 is used to gauge the second timing period. The vaporizer 18 may then be removed from the hive 10.

There are severe risks involved with the use oxalic acid. Given its caustic effect on the eyes, skin and respiratory system, it's labeled with the highest degree of toxicity, "Category 1." As with all pesticides, caution must be taken when handling oxalic acid by using a respirator, goggles and gloves. One should also try to remain upwind from the vapor cloud that is made with the vaporizer 18.

The prior art oxalic acid vaporizers have problems. Unknown, weak and unregulated car or vehicle battery connections to the vaporizer heating elements can affect the efficiency and complete vaporization in a timely manner. The necessity of a timer for timing two vaporizer operational periods requires the undivided attention of the bee keeper making it most difficult if not impossible to vaporize more than one hive at a time. Thus oxalic acid vaporization of bee hives is dangerous to both beekeepers and bees, time consuming and requires devote attention.

SUMMARY OF THE INVENTION

An oxalic acid vaporizer for vaporizing oxalic acid crystals in a bee hive with a bee entrance for treatment to kill mites on bees and in the bee hive has a cup to hold oxalic acid crystals with a resistive heating element mounted on one end of an extension. A handle is mounted on the other end of an extension with internal resistive heating element wires passing from the heating element to an internal circuit board with a microcontroller. A rocker switch is mounted on the handle connected to the circuit board. An LED is mounted to the handle connected to the circuit board. An external electrical cord is connected to the circuit board and extends out of the handle with a positive battery post clamp and a negative battery post clamp which are adaptable to be connected to a 12 volt battery.

A principal object and advantage of the present invention is the simplicity of operation of the vaporizer in that the bee keeper simply loads the cup with oxalic acid, slides the cup end of the vaporizer into the hive, hooks up the clamps to the battery, depresses the rocker switch, watches the LED light and removes the vaporizer from the hive after the LED light turns off.

Another object and advantage is that the simple operation of the vaporizer permits the bee keeper to operate multiple vaporizers at once, removing them from the hives when the LED lights go off.

Another object and advantage is that the simple operation of the vaporizer with its fail safe operation will not burn the oxalic acid and will not allow the vaporizer to overheat after vaporization.

Another object and advantage is that the simple operation of the vaporizer simply requires only the observance of the LED light and no need for timers.

Another object and advantage is that the simple operation of the vaporizer which is slid into the bee hive up to and abutting the handle to assure proper placement for oxalic acid vaporization within the bee hive.

Another object and advantage is the operation of the vaporizer is automatic with controlled heating once the rocker switch is activated to allow the bee keeper to tend to other hives and automatically shuts off to avoid excessive exposure to oxalic acid and excessive heat exposure to the bees which may cause bee fatalities.

BRIEF DESCRIPTION OF THE DRAWINGS

FIG. 1 is a front perspective view of a prior art and current bee hive;

FIG. 2 is a front perspective view of a prior art oxalic acid vaporizer:

FIG. 3 is a front perspective view of a prior art one gram scoop for measuring oxalic acid crystals;

FIG. 4 is a front perspective view of a prior art timer;

FIG. 5 is a top perspective view of the oxalic acid vaporizer of the present invention with a 12 volt battery;

FIG. 6 is a top plan view of the present invention;

FIG. 7 is a side elevational view of the present invention;

FIG. 8 is a top plan view of the circuit board of the present invention;

FIG. 9 is a front perspective view of the vaporizer of the present invention being inserted into a bee hive;

FIG. 10 is a front perspective view of the vaporizer of the present invention inserted into a bee hive, partially broken away, up to the handle of the vaporizer.

DETAILED SPECIFICATION

Figure 11:
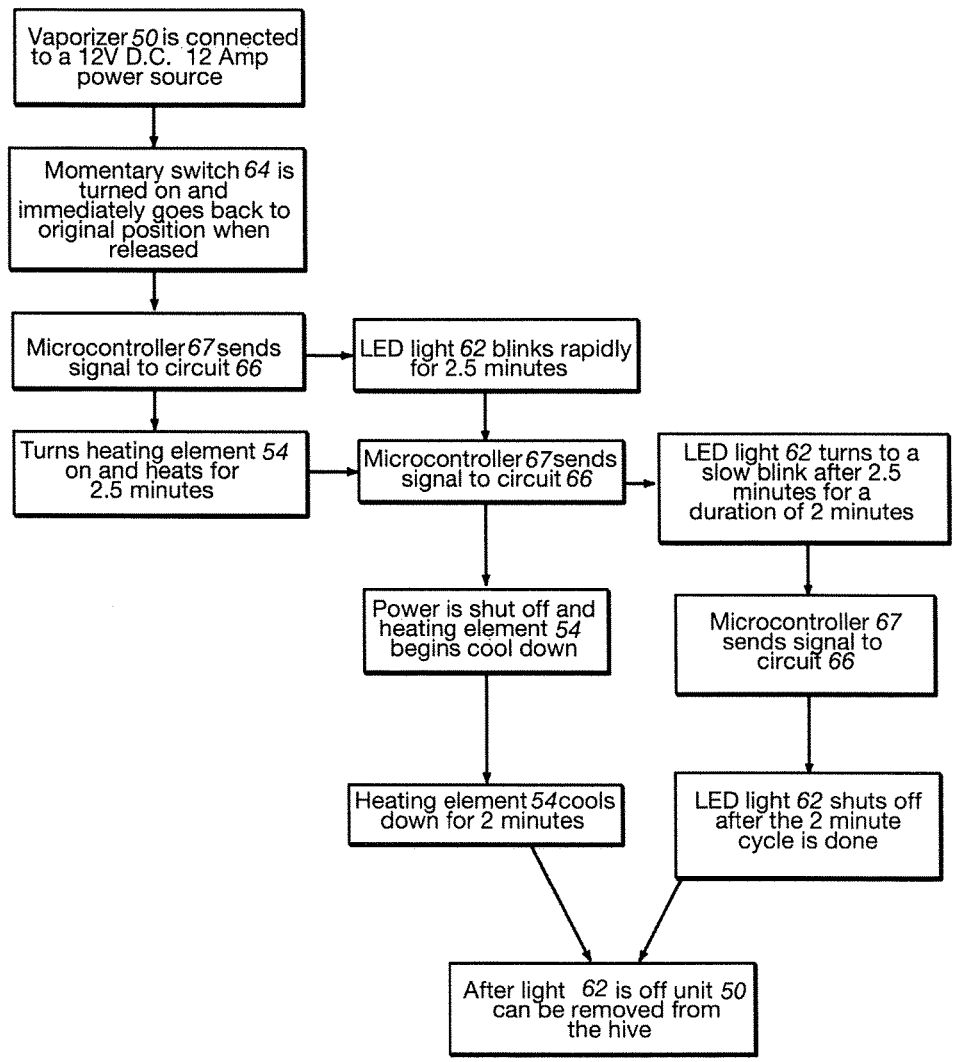
FIG. 11 is a flow chart of the operation of the present invention.

Referring to FIGS. 5 through 8 the construction oxalic acid vaporizer 50 of the present invention maybe understood. The vaporizer 50 has a cup or crucible 52 with an internal resistive heating element 54 mounted on one end of the extension 56. Internal wires 58 extend within the extension 56 from the heating element 54. A handle 60 is on the other end of the extension 56 and is generally of a larger size or diameter than the rest of the extension 56. A visible LED light 62 is mounted on or in the handle 60. A rocker switch 64 is also mounted on the handle 60. Within handle 60 is an internal circuit board 66.

The internal heating element wires 58, the LED light 62 and the rocker switch 64 are electrically connected to the circuit board 66 as shown in FIG. 8. Extending outwardly from the circuit board 66 and vaporizer 50 is an external cord 68 covering two wires that terminate at one positive battery post clamp 70 and one negative battery post clamp 72. A conventional car-type 12 volt battery 74 (FIG. 5) energizes the operation of the vaporizer 50. The positive battery post clamp 70 must be connected the battery 74 positive post 76 and the negative battery post clamp 72 must be connected to the battery negative post 78. Without this proper connection, the microcontroller or processor 67 on the circuit board 66 will not permit the vaporizer 50 to operate.

FIGS. 9 and 10 generally show the operation of the vaporizer 50 within the hive 10. The vaporizer 50 is set up to operate by removing the entrance reducer 14 and hooking up the battery clamps 70 and 72 properly to a 12 volt battery. Next, 1 gram of oxalic acid is placed in the vapor cup 52 with the aid of the measuring scoop 40. The cup 52 end of the vaporizer 50 is inserted into the entrance 12 located at the bottom of the hive 10 up to the handle 60 which is too large to pass into the entrance 12. Towels 80, rags or the like are used to seal up the hive 10 to assist in containment of the oxalic acid vaporize which is harmful to humans.

The operation of vaporizer is generally shown in flow chart FIG. 11 after the setup of the vaporizer 50 is complete. First, the rocker switch 64 is turned on afterwhich the switch 64 returns to its original off position. The LED light 62 flashes rapidly for about 2.5 minutes as the oxalic acid is vaporized into the hive 10 from the cup 52. Thereafter, the LED light 62 flashes slowly for 2 more minutes as the cup 52 cools down and the vapor is disbursed throughout the hive 10 with or without bees therein. The vapor crystalizes on everything including the bees and kill mites all while not harming the bees. When LED light 62 stops flashing slowly and turns off, the 2 minutes are up and the towels 80 and vaporizer 50 may be removed from the hive 10.

The above description is intended as illustrative and the true scope of the present invention is defined by the following claims.

What is claimed:

1. An oxalic acid vaporizer for vaporizing oxalic acid crystals in a bee hive with a bee entrance for treatment to kill mites on bees and in the bee hive, comprising:

a) a cup to hold oxalic acid crystals with a resistive heating element, the cup and the resistive heating element together being mounted on one of two ends of an extension;

b) a handle larger in size than the extension and adapted to be larger in size than the bee entrance, the handle mounted on the other end of the extension with internal resistive heating element wires passing from the heating element to an internal circuit board in the handle with a microcontroller on the circuit board to control and manage the operation of the vaporizer;

c) a rocker switch on the handle, the switch being connected to the circuit board wherein the switch returns to its original position once depressed;

d) an LED light is mounted to the handle, the LED light being connected to the circuit board wherein the microcontroller causes the LED light to flash rapidly for 2.5 minutes as the cup is heated to vaporize the oxalic acid crystals and then the LED light to flash slowly for 2 minutes as the cup cools down and the oxalic acid vapor is dispersed throughout the hive; and e) an external electrical cord connected to the circuit board and extending out of the handle, the external electrical cord being connected to a distal positive battery post clamp and a distal negative battery post clamp adaptable to be connected to a 12 volt, 12 amp battery.

2. A method of operating an oxalic acid vaporizer for vaporizing oxalic acid crystals in a bee hive with a bee entrance for treatment to kill mites on bees and in the bee hive, the vaporizer having a cup to hold oxalic acid crystals with a resistive heating element, the cup and the resistive heating element together being mounted on one of two ends of an extension, a handle mounted on the other end of the extension with internal resistive heating element wires passing from the heating element to an internal circuit board with a microcontroller in the handle, a switch on the handle, the switch being connected to the circuit board, an LED light is mounted to the handle, the LED light being connected to the circuit board; and an external electrical cord connected to the circuit board and extending out of the handle, the external electrical cord being connected to two distal clamps adaptable to be connected to a 12 volt, 12 amp battery, the method comprising:

a) connecting the vaporizer to the 12 volt, 12 amp battery with the clamps;

b) loading the cup with one gram of oxalic acid crystals;

c) placing the cup through the entrance of the hive;

d) activating the switch to energize the circuit board and the microcontroller to manage the operation of the vaporizer;

e) turning on the heating element for approximately 2.5 minutes and vaporizing the oxalic acid crystals;

f) turning on the LED light to flash rapidly for approximately 2.5 minutes;

g) turning off the heating element and flashing the LED light slowly for approximately 2 minutes; and h) turning off the LED light and removing the vaporizer from the hive.

* * * * *